(12) United States Patent
Augustine et al.

(10) Patent No.: US 6,585,670 B2
(45) Date of Patent: *Jul. 1, 2003

(54) TREATMENT APPARATUS WITH A HEATER ADHESIVELY JOINED TO A BANDAGE

(75) Inventors: Scott D. Augustine, Bloomington, MN (US); Keith J. Leland, Plymouth, MN (US); John P. Rock, Minneapolis, MN (US); Donald E. Stapf, Minneapolis, MN (US)

(73) Assignee: Augustine Medical, Inc., Eden Prairie, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/196,875

(22) Filed: Jul. 15, 2002

(65) Prior Publication Data

US 2002/0183813 A1 Dec. 5, 2002

Related U.S. Application Data

(63) Continuation of application No. 09/493,546, filed on Jan. 28, 2000, now Pat. No. 6,436,063, which is a continuation of application No. 09/055,597, filed on Apr. 6, 1998, now Pat. No. 6,071,304.

(51) Int. Cl.$^7$ ................................................. A61F 7/00
(52) U.S. Cl. .............................. 602/2; 602/14; 607/96; 607/114
(58) Field of Search ........................ 602/2, 14; 607/96, 607/108–112, 114

(56) References Cited

U.S. PATENT DOCUMENTS

| | | |
|---|---|---|
| 5,662,624 A | 9/1997 | Sundstrom et al. |
| 5,817,145 A | 10/1998 | Augustine et al. |
| 5,954,680 A | 9/1999 | Augustine |
| 5,964,723 A | 10/1999 | Augustine |
| 5,986,163 A | 11/1999 | Augustine |
| 6,071,304 A * | 6/2000 | Augustine et al. .............. 602/2 |
| 6,080,189 A | 6/2000 | Augustine et al. |
| 6,093,160 A | 7/2000 | Augustine et al. |
| 6,095,992 A | 8/2000 | Augustine |
| 6,110,197 A | 8/2000 | Augustine et al. |
| 6,213,965 B1 | 4/2001 | Augustine et al. |
| 6,235,047 B1 | 5/2001 | Augustine et al. |
| 6,436,063 B1 * | 8/2002 | Augustine et al. ............ 602/14 |

FOREIGN PATENT DOCUMENTS

WO        WO 94/0090        1/1994

* cited by examiner

Primary Examiner—Robert L. Nasser
(74) Attorney, Agent, or Firm—Gray Cary Ware & Freidenrich; Terrance A. Meador

(57) ABSTRACT

A wound treatment apparatus is provided which includes a thermally conductive bandage, a heater in contact with the bandage over a wound treatment area, and an adhesive attachment device for maintaining thermally conductive contact between the heater and the bandage. The bandage and heater together have a low profile so as to be convenient for the patient and are flexible so as to conform to the shape of the wound and to the contours of the skin surrounding the wound. The attachment device is fashioned so as to have less pull strength than an adhesive holding the bandage to the person's body so that the heater can be easily removed without disturbing the attachment of the bandage to the person's body. The bandage is provided with a polymeric film for maintaining moisture at the wound site as well as enhancing the utility of the attachment device.

49 Claims, 13 Drawing Sheets

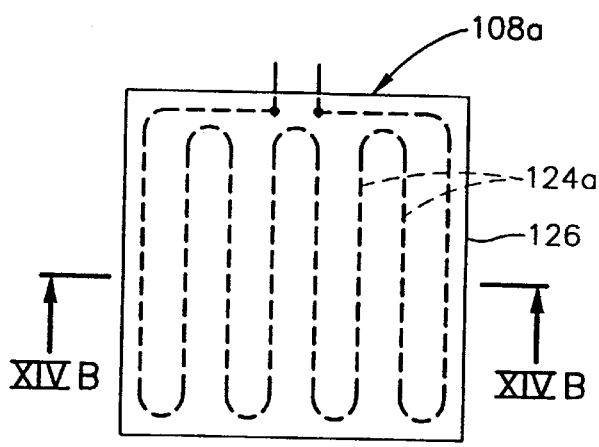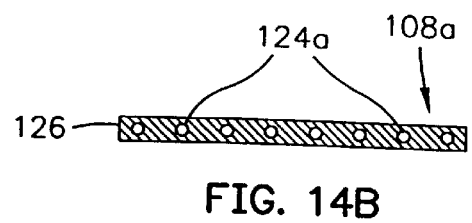
FIG. 14A
FIG. 14B
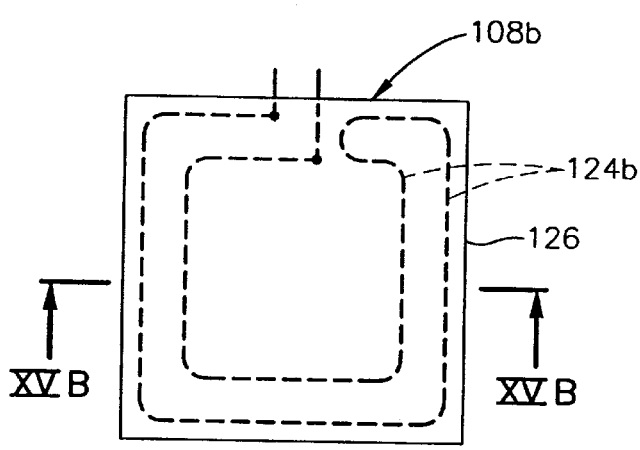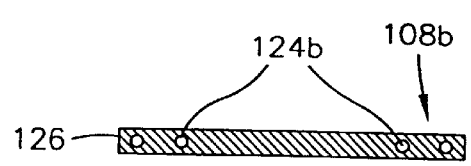
FIG. 15A
FIG. 15B
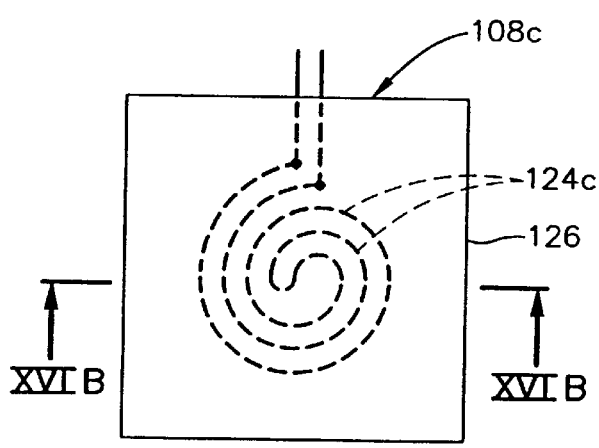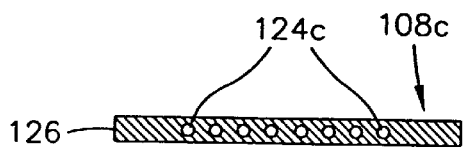
FIG. 16A
FIG. 16B

TREATMENT APPARATUS WITH A HEATER ADHESIVELY JOINED TO A BANDAGE

CROSS-REFERENCES TO RELATED PATENT AND COPENDING APPLICATIONS

This application is a continuation application of U.S. application Ser. No. 09/493,546, filed Jan. 28, 2000, now U.S. Pat. No 6,436,063, which is a continuation application of U.S. application Ser. No. 09/055,597, filed Apr. 6, 1998, now U.S. Pat. No. 6,071,304.

This application contains material related to U.S. patent application Ser. No. 08/843,072 filed on Apr. 11, 1997 entitled "FLEXIBLE NON-CONTACT WOUND TREATMENT DEVICE WITH A SINGLE JOINT", now U.S. Pat. No. 6,110,197, and to the following commonly assigned pending U.S. patent applications:

Ser. No. 07/900,656, filed Jun. 19, 1992, for "THERMAL BODY TREATMENT APPARATUS AND METHOD", now abandoned;

Ser. No. 08/342,741, filed Nov. 21, 1994, for WOUND TREATMENT DEVICE", now U.S. Pat. No. 5,817,145;

Ser. No. 08/356,325, filed Feb. 21, 1995, for "WOUND COVERING", now abandoned;

Ser. No. 08/785,794, filed Jan. 21, 1997, for "NORMOTHERMIC HEATER WOUND COVERING", now U.S. Pat. No. 5,986,163;

Ser. No. 08/786,713, filed Jan. 21, 1997, for "NORMOTHERMIC TISSUE HEATING WOUND COVERING", now U.S. Pat. No. 5,964,723;

Ser. No. 08/786,714, filed Jan. 21, 1997, for "NEAR HYPOTHERMIC HEATER WOUND COVERING", now U.S. Pat. No. 5,954,680; and Ser. No. 08/838,618, filed Apr. 11, 1997, for "FLEXIBLE NON-CONTACT WOUND TREATMENT DEVICE", now U.S. Pat. No. 6,093,160;

This application also contains material related to the following commonly assigned U.S. patent applications:

Ser. No. 09/056,191, filed Apr. 6, 1998, for "WOUND TREATMENT APPARATUS WITH A HEATER, A HEAT CONDUCTIVE BANDAGE, AND A HEAT-SPREADING MEANS ACTING BETWEEN THE HEATER AND BANDAGE", now U.S. Pat. No. 6,235,047;

Ser. No. 09/055,725 filed Apr. 6, 1998 for "WOUND TREATMENT APPARATUS WITH INFRARED ABSORPTIVE WOUND COVER", now U.S. Pat. No. 6,213,965;

Ser. No. 09/056,063 filed Apr. 6, 1998 for "WOUND TREATMENT APPARATUS WITH IR-TRANSPARENT OR IR-TRANSMISSIVE WOUND COVER", now U.S. Pat. No. 6,080,189; and Ser. No. 09/055,605 filed Apr. 6, 1998 for "WOUND TREATMENT APPARATUS FOR NORMOTHERMIC TREATMENT OF WOUNDS", now U.S. Pat. No. 6,095,992.

STATEMENT OF REGARDING FEDERALLY SPONSORED RESEARCH OR DEVELOPMENT

Not Applicable

REFERENCE TO A MICROFICHE APPENDIX

Not Applicable

BACKGROUND OF THE INVENTION

1. Field of the Invention

The present invention relates to a wound treatment device with a bandage and heater that are essentially planar, yet flexible, and are connected or joined by an attachment device that promotes heat transfer from the heater to the bandage and permits removal of the heater from the bandage while the bandage remains on the patient.

2. Description of the Related Art

Wounds, in general, are breaks in the integrity of the skin of a patient. A first type of wound may result from mechanical trauma that produces a cut, tear, or an abrasion. There are many instruments of causality for such wounds, including knives, glass, gravel, or a scalpel. A second type of wound may be caused by a combination of heat and pressure wherein the heat alone is insufficient to cause an outright burn. Such wounds include pressure sores, decubitus ulcers, or bed sores, and reflect an injury that is chronic in nature. A wound may also be vascular in origin. In this third type of wound, blood flow through a region may be altered sufficiently to cause secondary weakening of tissues which are eventually disrupted, thus forming a wound. In the case of arterial causes, the primary difficulty is getting oxygenated blood to the affected area. For venous causes, the primary difficulty is fluid congestion in the affected area which backs up, decreasing the flow of oxygenated blood. Because these wounds manifest underlying chronic disease processes, such as atherosclerotic vascular disease, congestive heart failure, and diabetes, these vascular injuries also are chronic in nature, forming wounds with ulcerated bases.

Heat therapy has been used to treat wounds since the days of Hippocrates, with varying results. Up to now, heat therapy for wounds has involved the application of heat under conditions that make the tissues of a wound hyperthermic. Hyperthermia impedes wound healing and may actually damage the wound tissues.

The "normal" range of temperature for the human body is in the range of 37° C.±1° C. (36° C.–38° C.). This is termed the "normothermic" range. Humans exhibit a thermoregulatory response to core temperature changes as little as ±0.1° C., wherein "core" as used herein refers to interior portions of the body. This extremely tight temperature control is necessary because virtually all cellular functions, chemical reactions and enzymatic reactions are optimum at normothermia.

Surface tissue varies in temperature according to whereon the body it is located. The skin of the torso is usually hypothermic, while the skin of the legs is always hypothermic. The normal skin temperature of the distal leg is approximately 32° C., which is considered to be "moderately hypothermic". The skin temperature of the distal leg of a patient with vascular insufficiency may be as low as 25° C., which is "severely hypothermic". The hypothermic condition of wounds and ulcers inhibits healing. Severely hypothermic skin or wound tissue is in a state that may be termed "suspended animation". In suspended animation, tissue is living, but cellular functions necessary for cell division and collagen deposition are slowed or even stopped. Further, the immune system is inhibited, allowing wounds to become heavily colonized with bacteria. The local application of heat to hypothermic skin will cause some degree of vasodilatation, resulting in an increase in local blood flow. Increased blood flow increases the subcutaneous oxygen tension ($PsqO_2$) which, in turn, increases both collagen deposition and immune function.

Many references report that the immune system is inhibited by hypothermia and activated by mild hyperthermia (fever). Persp Biol Med:439–474. Spring 1980, reports that local body temperature is a critical factor determining host susceptibility, the location of lesions and contracting infectious diseases. New Eng J Med 305:808–814, 1981, reports that animals exposed to cold environments are more susceptible to infectious diseases, whereas exposure to high ambient temperatures often produces a beneficial result. Wound Rep Reg 2:48–56, 1994 and Acta Anaesth Scand 38:201–205, 1994, report that infections caused by a standard inoculum of *e. coli* or *s. aureus* were significantly more severe in hypothermic guinea pigs than in normothermic control animals. New Eng J Med 334:1209–1215, 1996, reports that hypothermic colorectal surgical patients had three times more wound infections (19% vs. 6%) than those who were kept normothermic during surgery with a Bair Hugger® patient warming system described in commonly assigned U.S. Pat. Nos. 5,324,320, 5,300,102 and 5,350,417. Further, six weeks of warming therapy with the Bair Hugger® patient warming system has successfully healed chronic progressive ulcers which heretofore have been resistant to standard therapies.

Currently available medical devices that apply heat to wounds include infrared lights, warm water pads, warm water bottles, whirlpools and Sitz baths. All types of lesions, such as surgical, chronic, traumatic, donor sites, infected wounds and burns, have been treated with these warming modalities. Particularly difficult has been the application of heat to open wounds such as ulcers. Treatment of a wound with infrared light requires that the wound be positioned under the light during therapy, necessitating patient immobility. Further, the infrared heat causes the wound to dry, thereby slowing the healing process. Warm water pads and bottles and electrical heating pads are cumbersome, reduce patient mobility, and are usually applied to the extremities and held in place with inconvenient wraps such as straps, hook-and-eye material or tabs. Whirlpools and Sitz baths reduce mobility and limit the duration of warming therapy due to skin maceration by the water. None of these modalities is capable of prolonged heat treatment of a wound.

SUMMARY OF THE INVENTION

There is a need for a wound treatment apparatus to conveniently treat a wound with heat therapy for a prolonged period of time, while allowing patient mobility. It is also important that the wound treatment apparatus be flexible and have a low profile for convenience of the patient. Such a wound treatment apparatus should be thermally conductive for efficient heat transfer, be convenient to operate without adversely impacting the patient, and be capable of maintaining a moist wound environment.

Preferably, the operation of the wound treatment apparatus is referred to a "wound treatment area" (or "treatment area") that may include the wound, unwounded skin adjacent the wound (the periwound), or both.

In order to deliver heat therapy to a wound treatment area it would be beneficial to employ standard bandages that are available for wound treatment. In this case, a heater may conveniently be placed on top of such a bandage and the heater/bandage apparatus may be placed on the wound treatment area. The heater and bandage are joined by an adhesive attachment device.

The bandage should preferably just cover the treatment area. Attachment of the bandage to a person's body then becomes an important variable if the heater must be removed while the bandage remains in place. That is, removal of the heater should not disturb the attachment of the bandage to the person's body. This requires consideration of attachment devices that act between the heater and the bandage and between the bandage and the person's body.

The bandage is preferably thermally conductive. Thermally conductive bandages may be made of such materials as hydrogels, hydrocolloids, moist gauze, moist foam, hydrated alginates and polymeric films. In a preferred embodiment, an upper surface of the bandage includes a layer of moisture-impermeable material. With this arrangement, the bandage protects and maintains the humidity of the wound bed and the adjacent tissue.

The heater may be fashioned to primarily heat the wound, to primarily heat the periwound area, or to heat both the wound and the periwound area. Exemplary heat sources are electrical resistance heaters, chemical heaters, water pad heaters and phase-change salt heaters. In one embodiment of the invention, electrical resistance elements are embedded in or laminated to a flexible film, such as silicon, flexible rubber or flexible cloth. With this arrangement the heater is planar and flexible with a low profile. Alternatively, a water pad heater can be used. Such a heater may be made by thermo-forming two sheets of polymeric film into fluid channels and sealing the periphery. Warm water is then circulated through the pad by an external heater and pump. In other embodiments, a chemical heater or a phase-change salt heater may be used.

The attachment device may be made of a layer of polymeric film with a layer of adhesive applied to both sides which is commonly referred as "two-faced tape" or "double-sided tape". In another embodiment, a layer of adhesive is applied to a surface of the bandage and/or the heater. The attachment device may be continuous across the entire treatment area so that uniform bonding will promote uniform conductive heat transfer from the heater to the bandage. The attachment device employs an adhesive in contrast to straps, hook-and-eye material or tabs. These latter devices allow air spaces to develop between the heater and the bandage resulting in poor and unpredictable heat transfer to the wound.

In a preferred embodiment, the heater is detachable from the bandage when it is not in use. In one embodiment, this may be accomplished by making the adhesive between the heater and the bandage less tacky than the adhesive between the bandage and the skin. Alternatively, the adhesive applied to the double-sided tape, or to either or both of the surfaces of the heater and the bandage, can be arranged in an intermittent pattern so that its pull strength is less than the pull strength of the adhesive holding the bandage to the skin surface. In embodiments where the adhesive is applied to the surface of each of the heater and the bandage, the adhesive may be selected from a group of adhesives that are not tacky to the touch but will adhere to each other.

An object of the present invention is to provide an apparatus for treating wounds with heat which has a low profile for convenience of a patient, is flexible for mobility of the patient and transfers heat by conduction to a wound and/or periwound site so as to promote heat treatment thereof.

Another object is to provide a substantially planar wound treatment apparatus that conforms to the wound and the adjacent skin.

A further object is to provide a low profile and flexible wound treatment apparatus that provides heat transfer to a wound and is easy to operate without impacting the patient's comfort.

Still another object is to provide a low profile, flexible wound treatment apparatus that includes a heater attached to a bandage wherein the heater can be easily detached from the bandage without detaching the bandage from the skin of a patient.

Still a further object is to provide a highly mobile and convenient wound treatment apparatus which promotes heat transfer to a wound and which maintains a moist environment thereon.

Other objects and advantages of the invention will become apparent upon reading the following description taken together with the accompanying drawings.

DESCRIPTION OF THE DRAWINGS

FIG. 14A is a planar illustration of an electrical resistance element embedded in a flexible layer for uniform heating;

FIG. 14B is a view taken along plane XIVB—XIVB of FIG. 14A;

FIG. 15A is a planar view of an electrical resistance element embedded in a flexible layer for heating a portion of a treatment area;

FIG. 15B is a view taken along plane XVB—XVB of FIG. 15A;

FIG. 16A is a planar view of an electrical resistance element embedded in a flexible layer for uniform heating of a central portion of a treatment area;

FIG. 16B is a view taken along plane XVIB—XVIB of FIG. 16A;

DESCRIPTION OF THE PREFERRED EMBODIMENTS

Figure 1:
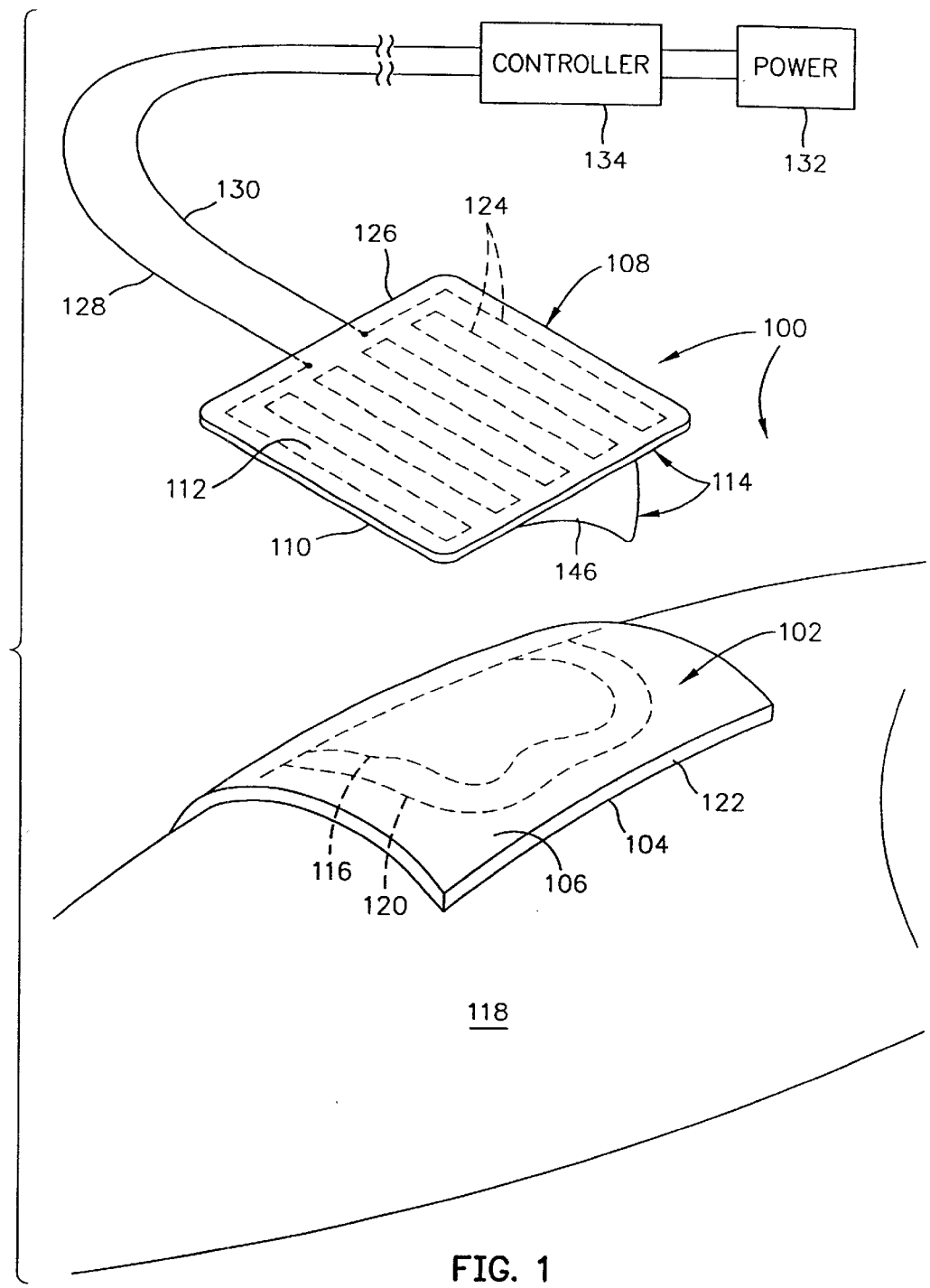
FIG. 1 is an isometric view of a first embodiment of the wound treatment apparatus being applied to a wound on a person's body.

Referring now to FIGS. 1–34, wherein like reference numerals designate like or similar parts throughout the several views there are shown various embodiments of a wound treatment apparatus in according to the invention.

Figure 2:
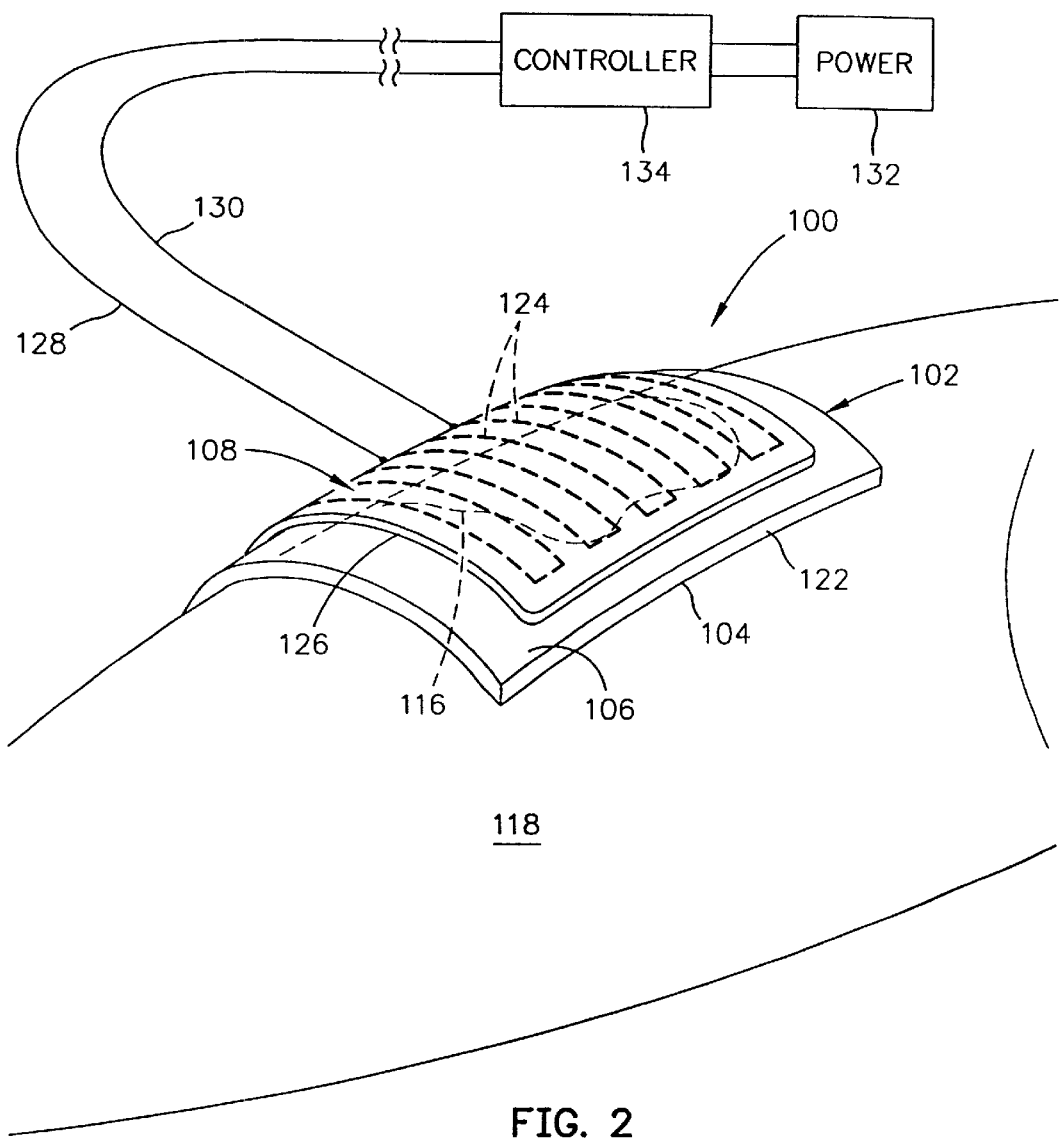
FIG. 2 is an isometric view of the wound treatment apparatus applied to the wound on the person's body.
Figure 3:
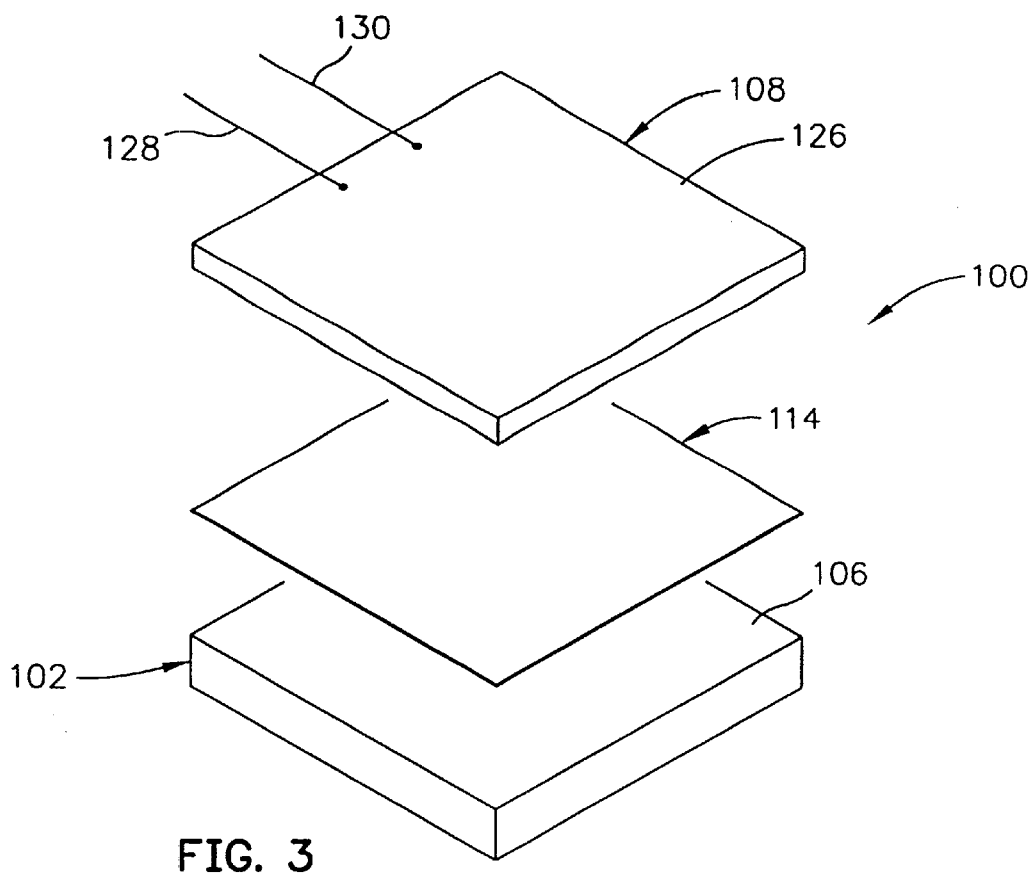
FIG. 3 is an exploded isometric view of the wound treatment apparatus.
Figure 4:
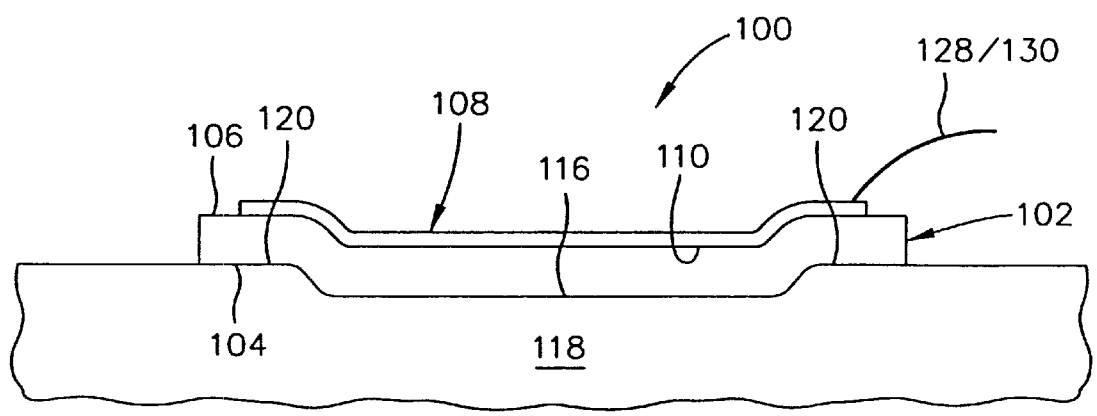
FIG. 4 is a cross-sectional view of the wound treatment apparatus applied to the wound on the person's body.

As shown in FIGS. 1–6, one embodiment of the wound treatment apparatus 100 includes a thermally conductive bandage 102 which has first (lower) and second (upper) surfaces 104 and 106, a heater 108 which has first (lower) and second (upper) surfaces 110 and 112 and an attachment device 114 for joining the heater 108 and the bandage 102 in such a manner as to transfer heat from the heater 108 to the bandage 102. Preferably, the attachment device maintains surface-to-surface contact between the second surface 106 of the bandage 102 and the first surface 110 of the heater. In FIGS. 2 and 4, the wound treatment apparatus 100 is shown in place covering a wound 116 of a person's body 118, the wound being shown depressed. Immediately adjacent the wound is a periwound area 120 which is typically a peripheral band of tissue around the wound area with less trauma than the tissue of the wound area. As will be explained in more detail hereinafter, the wound treatment apparatus is capable of treating a wound treatment area that includes the wound and/or the periwound area, as desired.

Figure 5:
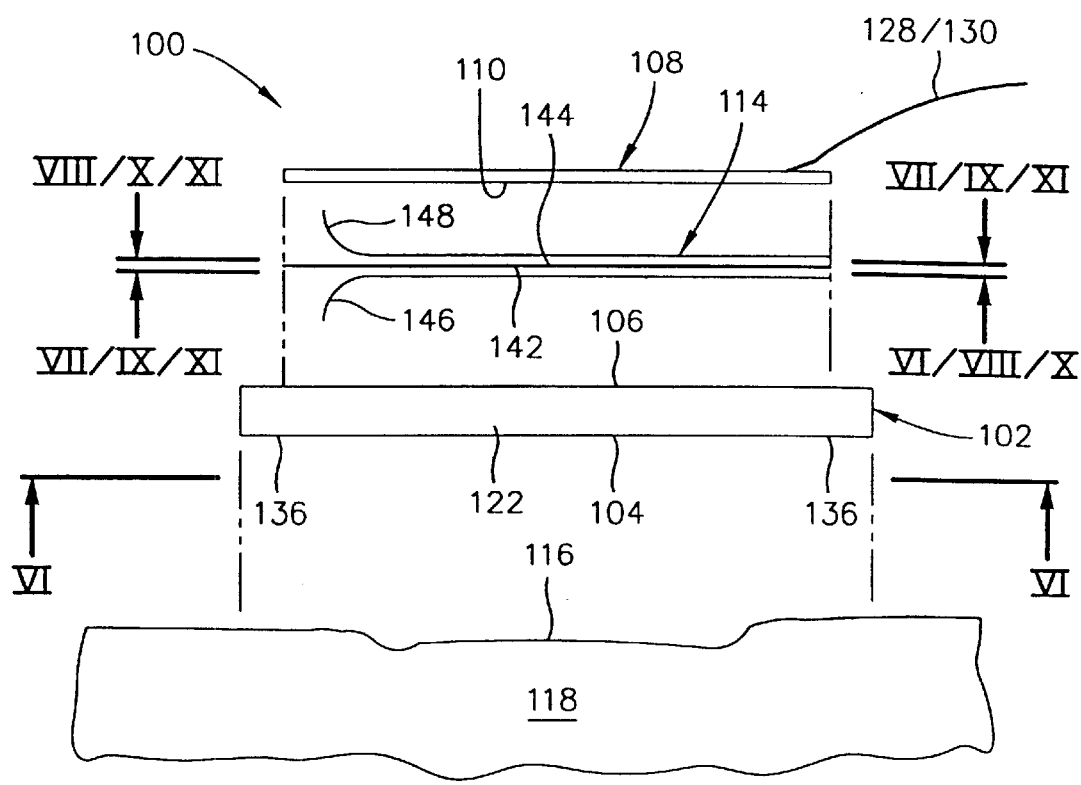
FIG. 5 is an exploded cross-sectional illustration of an embodiment of the invention above the wound area of the person's body.

The second surface 106 of the bandage preferably comprises a sheet of smooth material. In a preferred embodiment, this surface may be provided by a polymeric film. A layer 122 of hydrogel, hydrocolloid, or hydrated alginate may be affixed to the polymeric film 106 by any suitable means, such as an adhesive, and may provide the first surface 104. It is preferred that any of these combinations provide the bandage with high thermal conductivity and maintain a moist environment at the wound. In the layer 122, a foam or gauze may be used in lieu of the compounds enumerated above. If the gauze or foam provides the first surface 104, the gauze or foam will absorb moisture from the wound, providing the desired heat conductivity and moist environment. Alternatively, the bandage 102 may simply be a single layer or film of a heat-conductive polymer so as to optimize heat conductivity of the bandage. In any embodiment of the bandage, it is preferred that the bandage be planar, as shown in FIGS. 3 and 5, and be flexible to conform to the wound 116 as shown in FIG. 4, as well as the person's body, as shown in FIGS. 1 and 2.

In the embodiment 100 of the wound treatment apparatus, the heater 108 includes means for generating heat that may be electrically operated. For example, the means may take the form of an electrical resistance element 124 which is embedded in or laminated to a flexible planar member 126, such as polyethylene, silicon, rubber or flexible cloth. In the preferred embodiment, the heater 108 is substantially planar, as shown in FIGS. 1, 3 and 5, and yet flexible in order that it conform, with the bandage, to the wound 116, as shown in FIG. 4, and to the person's body as shown in FIGS. 2 and 4. As will be explained in more detail hereinafter, the adhesive attachment device 114 joins the heater 108 to the bandage 102, as shown in FIG. 4, so as to maximize heat transfer between the heater 108 and the bandage 102.

As illustrated in FIGS. 1 and 4, the electrical resistance element 124 is connected to first and second electrical conductors 128 and 130, which are connected to an electrical power source 132, via a controller 134. The purpose of the controller 134 is to control electrical power provided to the electrical resistance element 124 to maintain a normothermic temperature at or near the wound 116. As shown in FIGS. 1 and 2, the electrical resistance element 124 may extend back and forth in the flexible planar member 126 with a desired spacing to promote uniform heating of the heater 108.

Figure 6:
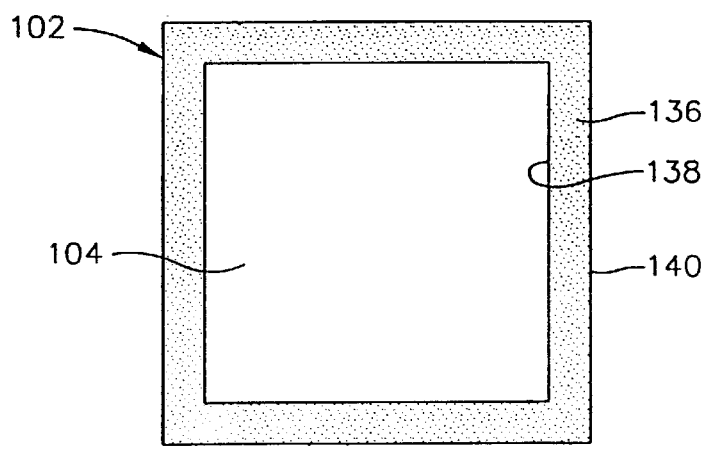
FIG. 6 is a view taken along plane VI—VI of FIG. 5.

As shown in FIG. 6, the first surface 104 of the bandage 102 is provided with an open pattern of adhesive 136 at or near its periphery. The adhesive pattern 136 may completely encompass the wound and the periwound area so as to trap the natural moisture of the body which, in turn, moistens the layer 122 of the bandage, or otherwise maintains a moist environment across the wound treatment area for wound therapy purposes. Accordingly, the pattern of adhesive 136 has inner and outer boundaries 138 and 140 wherein, in the preferred embodiment, the outer boundary 140 coincides with the outer perimeter of the bandage. It should be understood that the bandage 102, the heater 108, and the pattern of adhesive 136 may take various shapes, such as the square, shown in the drawings, or a rectangle, circle or ellipse, or any other regular or irregular shape depending upon various shapes of wound treatment areas.

The preferred adhesive attachment device 114 is a double-sided tape, as shown in FIG. 5. It is preferred that the double-sided tape be a polymeric film with first and second surfaces with first and second layers of adhesive 142 and 144 thereon. The double-sided tape comes with first and second release liners 146 and 148 which are removed so that the adhesive layers 142 and 144 can be joined to the second surface 106 of the bandage 102 and to the first surface 110 of the heater 108, respectively, as shown in FIGS. 1, 4 and 5. In FIG. 1, the release liner 146 is partially removed from the adhesive layer 142 (see FIG. 5) in preparation for attaching the heater 108 to the second surface 106 of the bandage 102. The double-sided tape 114 is very flexible and conducts heat between the heater 108 and the bandage 102. It is preferred that the planar dimensions of the double-sided tape 114 be the same as the planar dimension of the heater 108 so as to transfer heat from the entire first surface 110 of the heater 108 to the bandage 102. It should be noted that, because of the polymeric film 106 forming the second surface of the bandage 102, transfer of heat by conduction to the bandage 102 is promoted.

Figure 7:
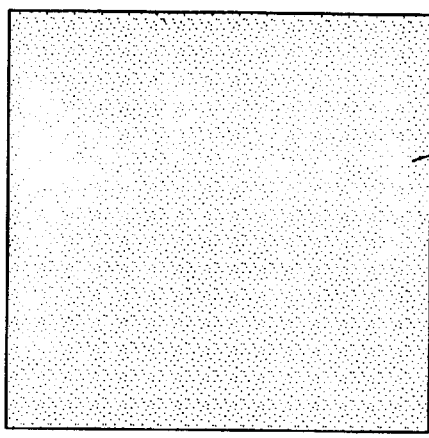
FIG. 7 is a view taken along plane VII—VII of FIG. 5.
Figure 8:
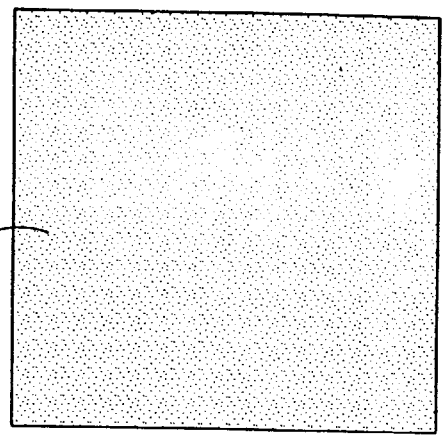
FIG. 8 is a view taken along plane VIII—VIII of FIG. 5.

When heat therapy is interrupted or terminated, it may be desirable to detach the heater 108 from the bandage 102. In this regard, the heater 108 is preferably detachably joined to the bandage 102. Detachment in the embodiment just described will necessitate pulling the heater 108 away from the bandage 102, thereby subjecting each adhesive layer therebelow to a pull force. In order for the bandage 102 to remain in place while the heater 108 is being removed, the pull strength of the attachment device 114 must be less than the pull strength of the pattern of adhesive 136. Various means for achieving this objective with double-sided tape are shown in FIGS. 7–12. FIGS. 7 and 8 show the adhesive layers 142 and 144 completely covering the surfaces of the polymeric film. One of these surfaces will be required to have less pull strength than the pull strength of the pattern of adhesive 136. In a preferred embodiment, the adhesive layer 142 has less pull strength than each of the pattern of adhesive 136 and the adhesive layer 144, allowing the heater 108 to be removed from the bandage 102 without leaving any adhesive on the bandage. This may be accomplished by employing an adhesive layer 142 which is less tacky than each of the pattern of adhesive 136 and the adhesive layer 144. Less tack can be achieved by doping the same adhesive with a solvent or inert filler, such as talcum or chalk, or employing another adhesive with a tack known to be less than the tack of the adhesives 136 and 144. If it is desired to leave the adhesive on the bandage 102, then the roles of the tack would be switched between the adhesive layers 142 and 144.

Figure 9:
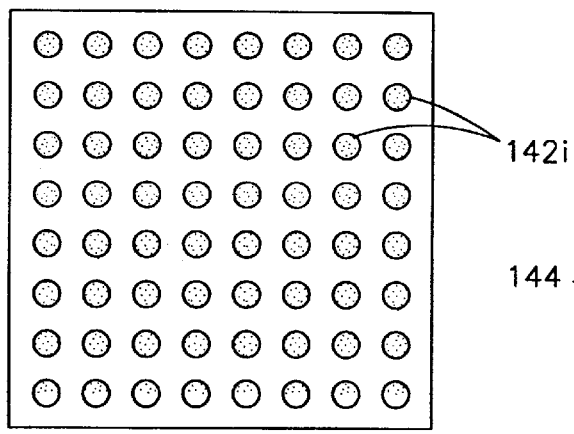
FIG. 9 is a view taken along plane IX—IX of FIG. 5.
Figure 10:
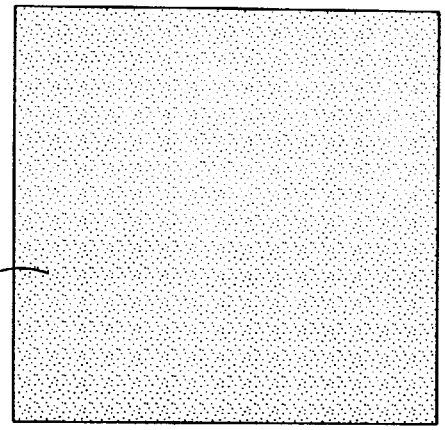
FIG. 10 is a view taken along plane X—X of FIG. 5.
Figure 11:
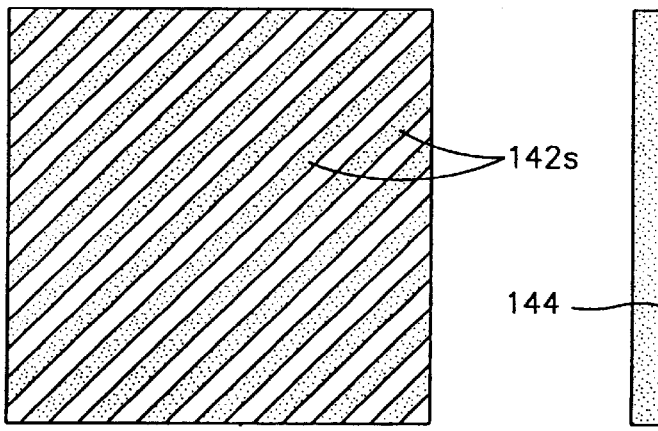
FIG. 11 is a view taken along plane XI—XI of FIG. 5.
Figure 12:
FIG. 12 is a view taken along plane XII—XII of FIG. 5.

Lower pull strength of the adhesive between the heater 108 and the bandage 102, as compared to the pull strength of the adhesive attaching the bandage 102 to a person's body, can be provided by intermittent adhesive patterns such as the circular regions 142*i* shown in FIG. 9. In contrast, as shown in FIG. 10, the adhesive layer 144 would be an entire plane so that when the heater is pulled, the double-sided tape leaves with the heater 108 rather than being retained on the bandage 102. As shown in FIG. 9, the adhesive regions 142*i* may be numerous circular dots of adhesive which are sized and spaced from one another in a matrix to provide a pull strength of the adhesive attachment device that is less than the pull strength of the pattern of adhesive 136 and less than continuous adhesive layer 144. With this arrangement, the same adhesive may be used for the adhesive layers 142 and 144 of the double-sided tape and the pattern of adhesive 136 on the bandage. Again, the layers 142 and 144 of the double-sided tape 114 may be switched if it is desired to leave the double-sided tape on the bandage 102 when the heater 108 is pulled therefrom. Another intermittent adhesive pattern is shown at 142*s* in FIG. 11, wherein diagonal spaced-apart strips of adhesive material are provided across the polymeric film. Here again, the sizing of the strips and their spacing from one another are arranged so that the pull strength of the adhesive attachment device is less than the pull strength of each of the pattern of adhesive 136 and the full plane adhesive layer 144 in FIG. 12. It should be understood that the intermittent adhesive structure may take various patterns in order to achieve the desired reduction in pull strength. The spacing between the intermittent layers should be made as small as possible so as to promote conductive heat transfer between the heater 108 and the bandage 102.

Figure 13:
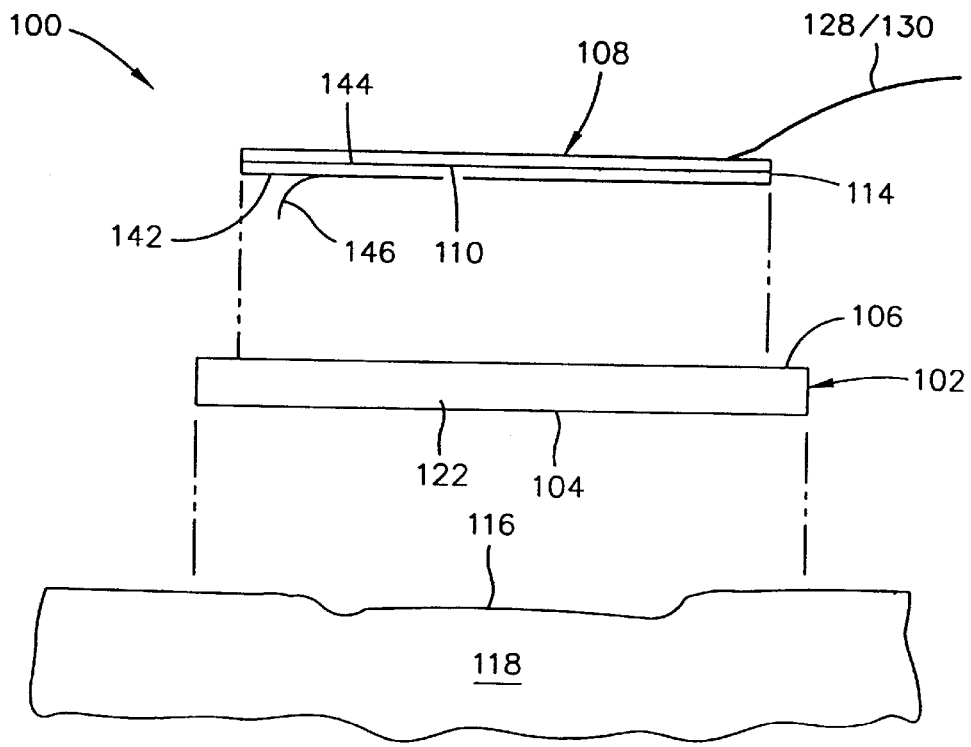
FIG. 13 is an exploded cross-sectional view of the first embodiment of the wound treatment apparatus after attaching an attachment device to the heater.

In FIG. 13 the adhesive layer 142 of the double-sided tape has been applied to the first surface 110 of the heater 108 and the release liner 146 has been partially removed from the first adhesive layer 142, similar to the showing in FIG. 1. The heater 108 may be supplied with the double-sided tape in place, as shown in FIG. 13, or may be supplied separately as described and shown in FIG. 5.

Manifestly, an attachment device should permit the heater and bandage to be joined in such a way as to maximize heat transfer therebetween while permitting the heater to be detached from the bandage without detaching the bandage from the skin. While various adhesive configurations are shown for this purpose, it is contemplated that other attachment mechanisms could be used.

FIGS. 14–16 illustrate various embodiments of electrical resistance heaters 108. Any of these embodiments are intended to be used in the embodiment of FIGS. 1 and 2. In the heater 108a shown in FIG. 14A, and electrical resistance element 124a winds back and forth within the flexible planar member 126, similar to what is shown in FIG. 1. The spacing between the windings of the electrical resistance element 124a may be sized so as to ensure substantially uniform heating. FIG. 14B shows the electrical resistance element embedded or laminated in the flexible planar member 126. In FIG. 15A, the electrical resistance element 124b takes a path along a peripheral zone of the flexible planar member 126, so that the periphery of the heater 108b is uniformly heated to a temperature greater than a central portion of the heater. Again, these electrical resistance elements 124b are shown embedded or laminated in the flexible planar member 126 in FIG. 15B. In FIG. 16A, the electrical resistance element 124c takes a spiral path out and back within a central region of the heater 108c so as to uniformly heat the central region of the heater to a higher temperature than regions outbound therefrom. The heater 108a is adapted for applying heat to both the wound and periwound area 116 and 120 in FIG. 4, the heater 108b is adapted for applying heat primarily to the periwound area 120 and the heater 108c is adapted for applying heat primarily to the wound 116.

Figure 17:
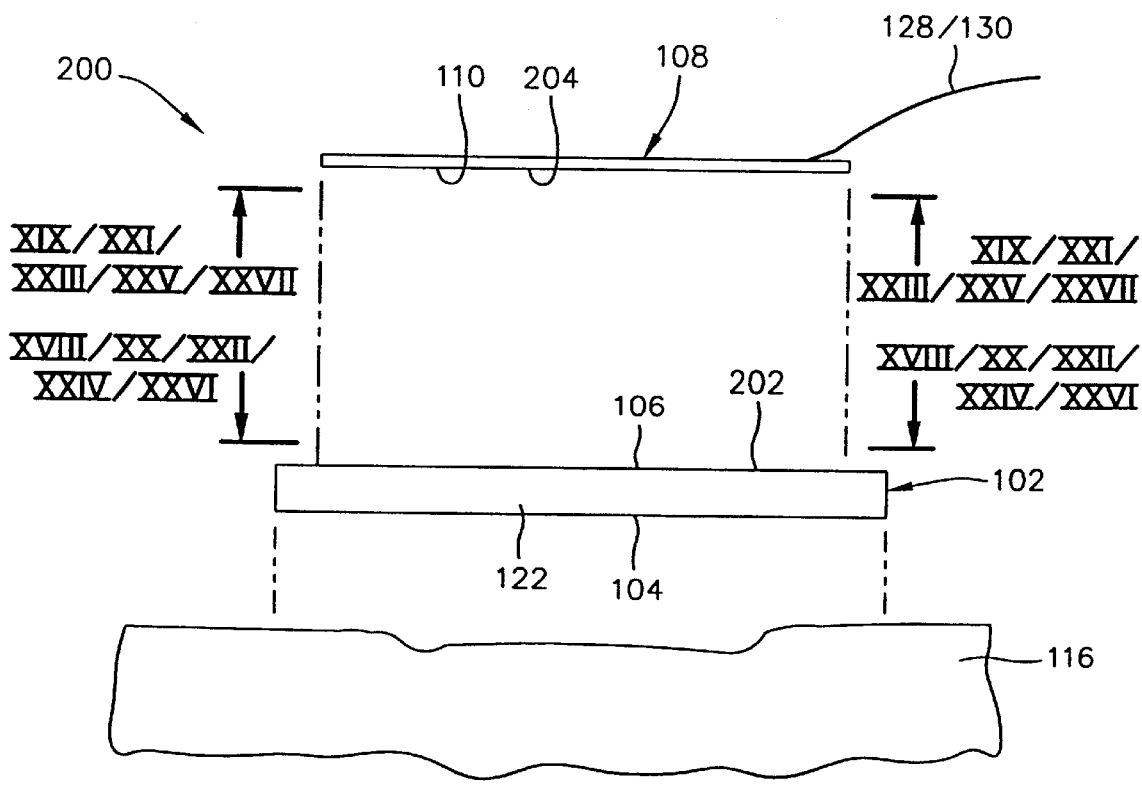
FIG. 17 is an exploded cross-sectional view of another embodiment of the invention shown above a wound area.
Figure 18:
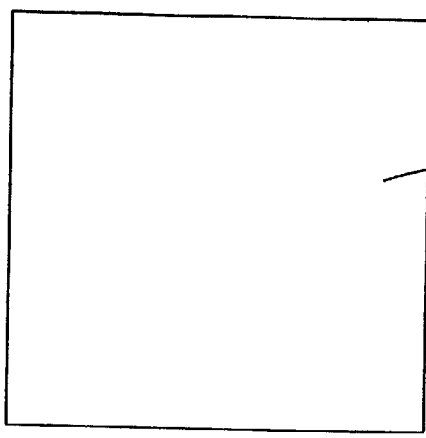
FIG. 18 is a view taken along plane XVIII—XVIII of FIG. 17.
Figure 19:
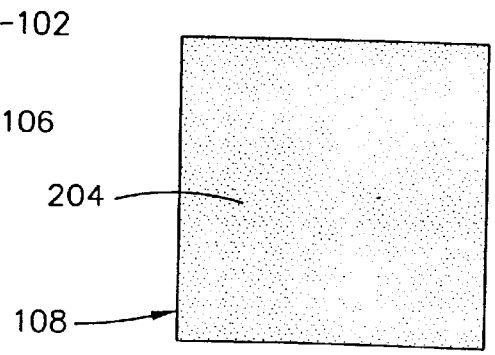
FIG. 19 is a view taken along plane XIX—XIX of FIG. 17.
Figure 20:
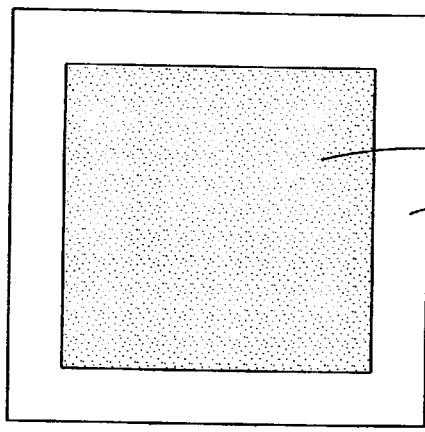
FIG. 20 is a view taken along plane XX—XX of FIG. 17.
Figure 21:
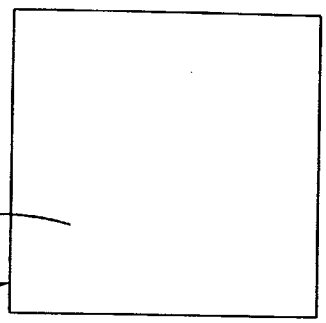
FIG. 21 is a view taken along plane XXI—XXI of FIG. 17.
Figure 22:
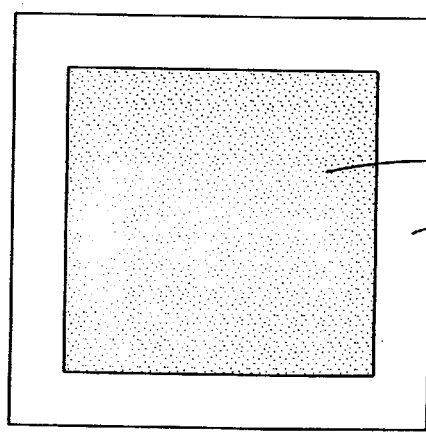
FIG. 22 is a view taken along plane XXII—XXII of FIG. 17.
Figure 23:
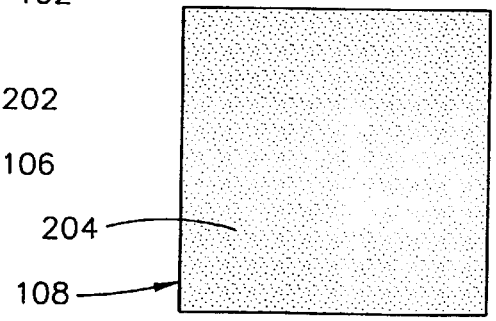
FIG. 23 is a view taken along plane XXIII—XXIII of FIG. 17.

Another embodiment 200 of the wound treatment apparatus is illustrated in FIG. 17, wherein an adhesive layer 202 is on the second surface 106 of the bandage 102 and/or an adhesive layer 204 is on the first surface 110 of the heater 108. Various embodiments of these attachment devices are illustrated in FIGS. 18–28. Various heater embodiments are illustrated in FIGS. 14A through 16B. The first embodiment of the attachment device is shown in FIGS. 18 and 19, wherein the heater 108 is provided with the adhesive layer 204 and the bandage 102 is not provided with any adhesive layer. In FIGS. 20 and 21, the situation is reversed wherein the bandage 102 is provided with the adhesive layer 202 and the heater 108 does not have an adhesive layer. FIGS. 22 and 23 illustrate a still further embodiment wherein the bandage 102 is provided with the adhesive layer 202 and the heater 108 is provided with the adhesive layer 204. The adhesive layers 202 and 204 in FIGS. 22 and 23 may be made from an adhesive which will bond only when these two adhesive layers are placed in contact with one another. Otherwise, the adhesive layer 204 will not bond to the polymeric surface surrounding the adhesive layer 202, or any other surface including a person's skin. This scheme has an advantage from the standpoint that adhesive layers 202 and 204 on the bandage 102 and the heater 108, respectively, will not attach to anything until they are brought into contact between the heater 108 and the bandage 102. This promotes manufacturability, logistics and operation of the invention. A suitable adhesive for this purpose is 3 M Non-Tacky Adhesive SJ-3101. It is desirable that the pull strength of the adhesive attachment devices shown in FIGS. 18–23 be lower than the pull strength of the body adhesive 136 shown in FIG. 6. This can be accomplished by making the tack of the adhesive attachment device less than the tack of the pattern adhesive 136.

Figure 24:
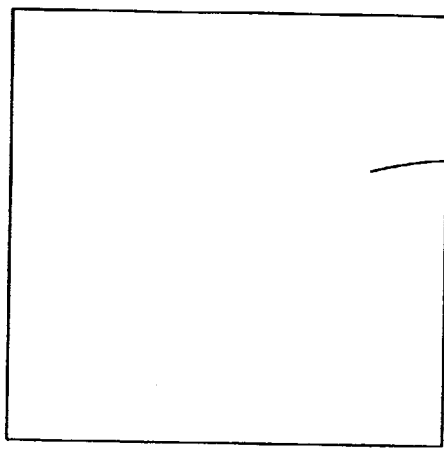
FIG. 24 is a view taken along plane XXIV—XXIV of FIG. 17.
Figure 25:
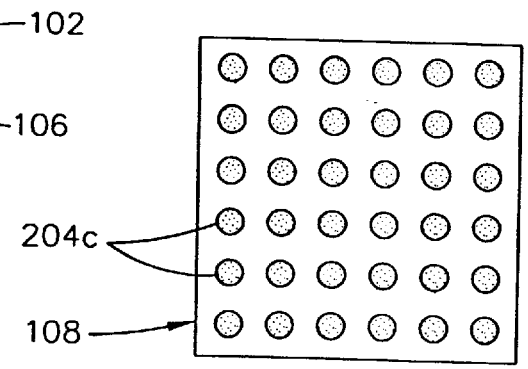
FIG. 25 is a view taken along plane XXV—XXV of FIG. 17.
Figure 26:
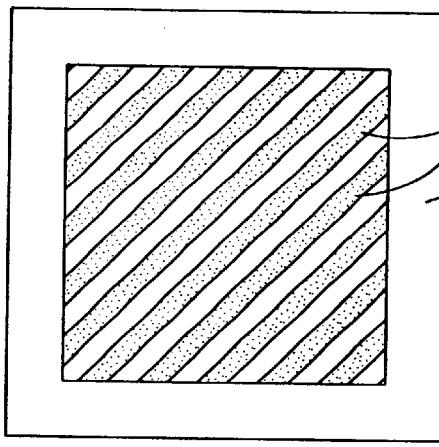
FIG. 26 is a view taken along plane XXVI—XXVI of FIG. 17.
Figure 27:
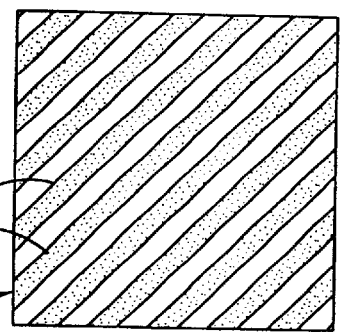
FIG. 27 is a view taken along plane XXVII—XXVII of FIG. 17.
Figure 28:
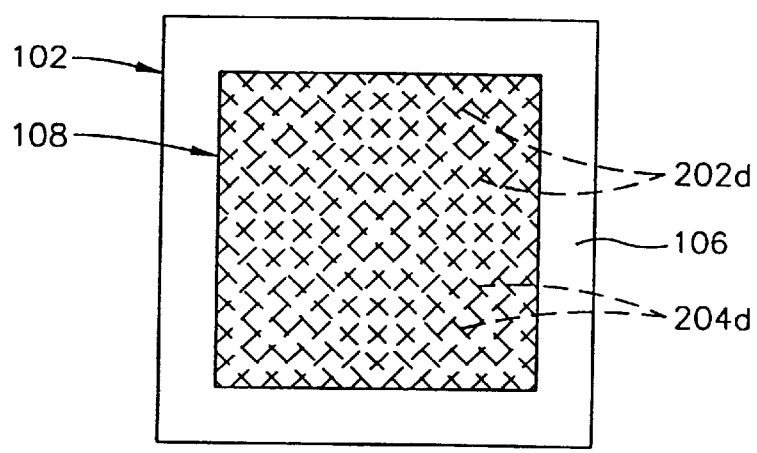
FIG. 28 is a view showing schematically the engagement of the intermittent adhesives shown in FIGS. 26 and 27.

Attachment devices employing intermittent adhesive patterns are shown in FIGS. 24–28. The embodiment in FIGS. 24 and 25 shows the heater 108 provided with circular spaced-apart adhesive regions 204c, while the bandage 102 is not provided with any adhesive. In the embodiment shown in FIGS. 26 and 27, each of the bandage 102 and the heater 108 is provided with diagonal spaced-apart adhesive strips 202d and 204d, respectively. When these adhesive strips are brought into contact with one another, as shown in FIG. 28, they criss-cross one another to provide the desired bonding between the heater 108 and the bandage 102.

The adhesive areas of the intermittent adhesive patterns shown in FIGS. 24–28 are sized and spaced from one another so that the pull strength of each attachment device is less than the pull strength of the pattern adhesive 136 shown in FIG. 6, as discussed hereinabove. Again, the size of the intermittent adhesive patterns and the spacing therebetween should be tailored to maximize thermal conductivity between the heater 108 and the bandage 102 and yet ensure that the pull strength between the heater and the bandage is less than the pull strength between the bandage and the person's body.

Figure 29:
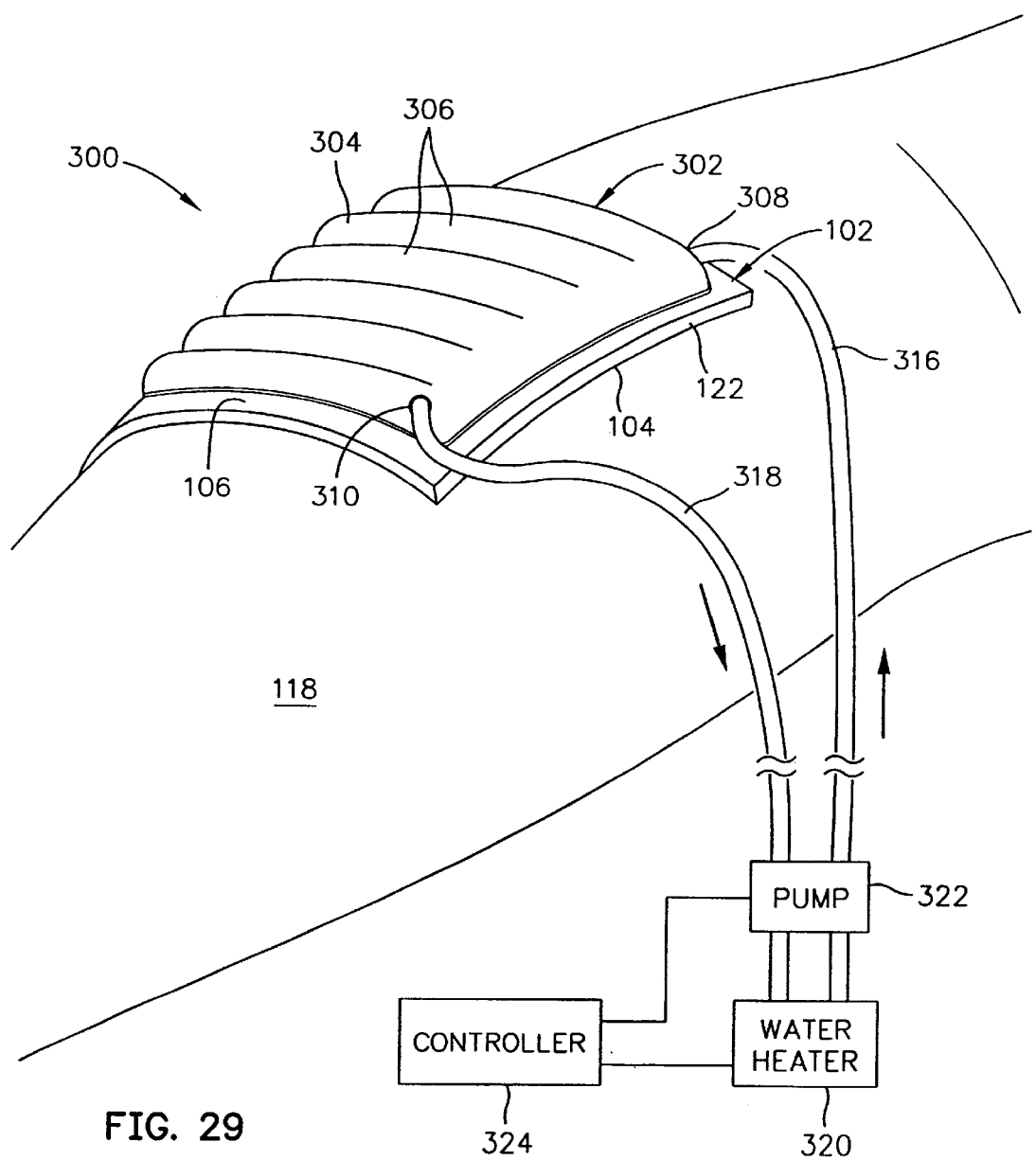
FIG. 29 is an isometric illustration of a further embodiment of the wound treatment apparatus applied to a wound on the person's body.
Figure 30:
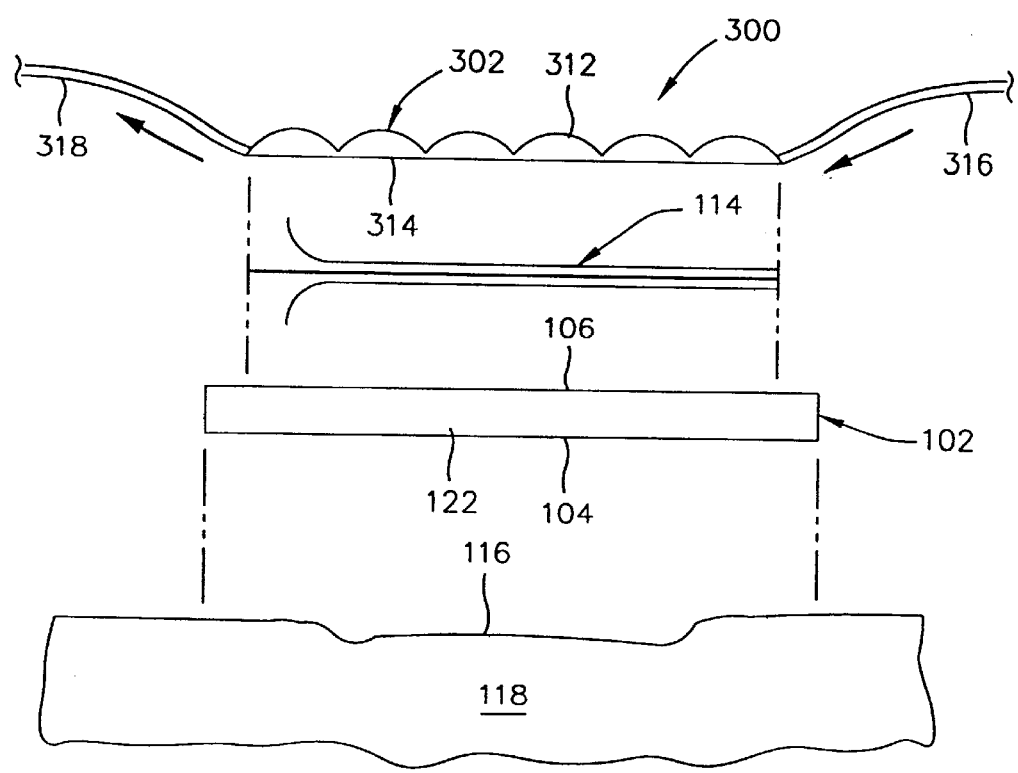
FIG. 30 is an exploded cross-sectional illustration of the apparatus shown in FIG. 29 shown above the wound.
Figure 31:
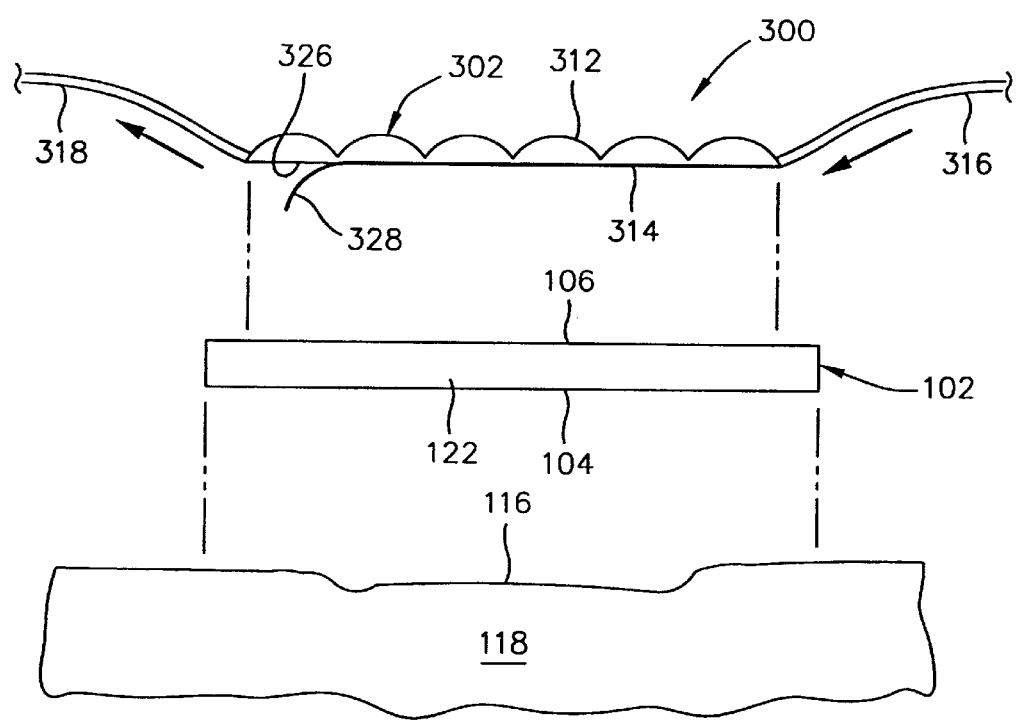
FIG. 31 is an exploded cross-sectional illustration of the FIG. 29 embodiment with an adhesive attachment device applied to the heater.

Another embodiment 300 of the wound treatment apparatus is illustrated in FIGS. 29–31. In this embodiment, a heater 302 employs heated water as the means for generating heat to be provided to the bandage 102. The heater 302 may comprise a pouch 304 which has water channels extending back and forth in series from an inlet end 308 to an outlet end 310. The pouch 304 may be made by thermo-setting the periphery as well as channel lines of a pair of polymeric films 312 and 314 as shown in FIG. 30. The bottom film 314 may be stiffer than the top film 312. Heated water is supplied by inlet and outlet water lines 316 and 318 which are connected to a water heater 320 via a pump 322. A controller 324 is provided for controlling the temperature of the water in the water heater 320 and the amount of water pumped by the pump 322. The heated water is preferably maintained at such a temperature and flow rate that the wound site 116 is maintained at or near a normothermic temperature. The bandage 102 may comprise any of the aforementioned embodiments. Further, the attachment device for attaching the heater 302 to the bandage 102 may comprise any of the aforementioned adhesive attachment devices. or any equivalent devices or arrangements that connect the heater and bandage for maximum thermal conductivity, yet allow detachment of the heater from the bandage without detaching the bandage from a patient's skin. The preferred attachment device is the double-sided tape 114 shown in FIG. 30, which has been described in detail hereinabove. Another suitable attachment device is shown in FIG. 31 wherein the water heater 302 is provided with an adhesive layer 326 and a release liner 328. The release liner 328 is simply pulled from the adhesive layer 326 and the adhesive layer 326 is employed for attaching the water heater 302 to the polymeric surface 106 of the bandage 102.

Figure 32:
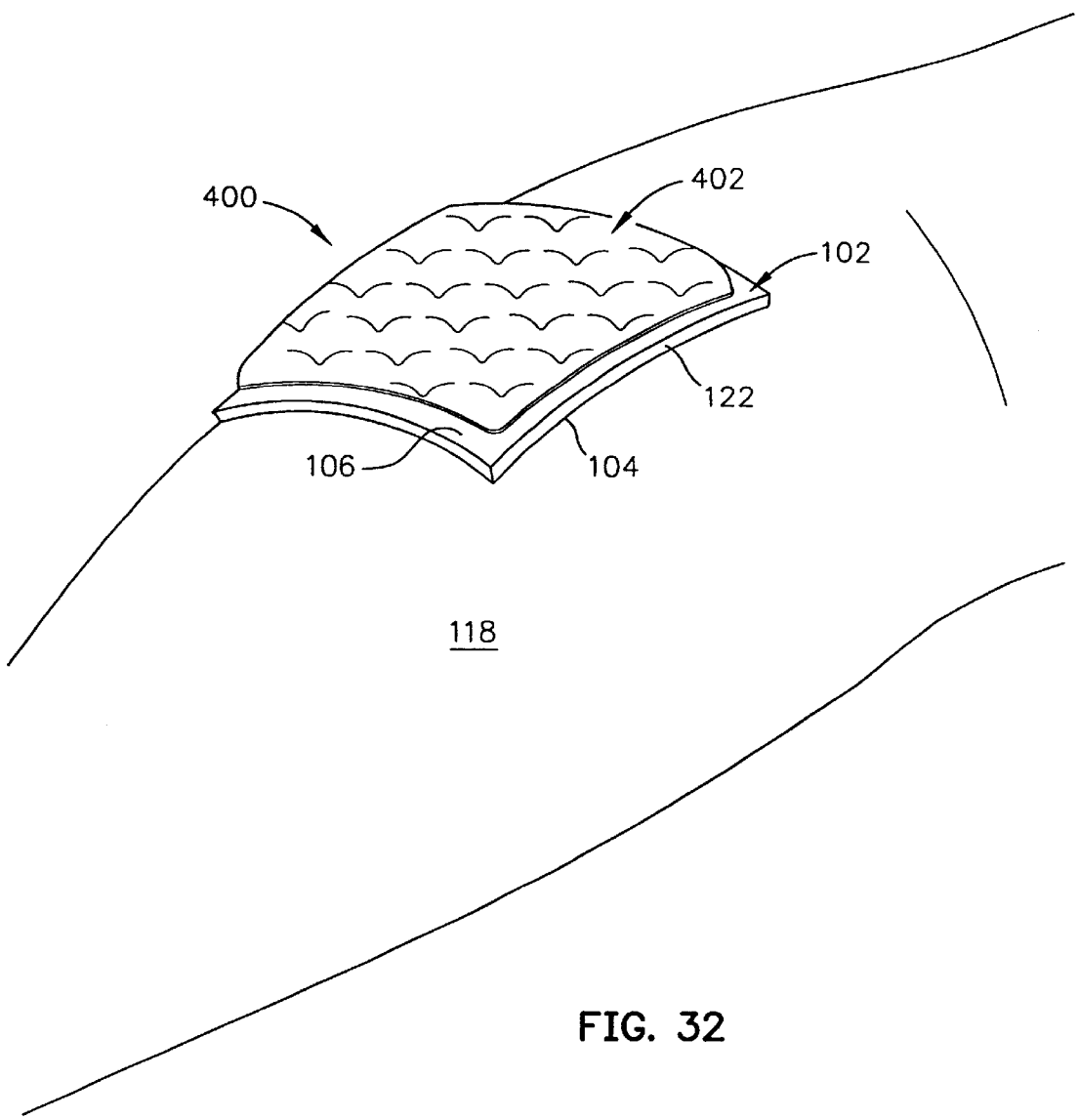
FIG. 32 is an isometric illustration of a still another embodiment of the invention applied to a wound on the person's body.
Figure 33:
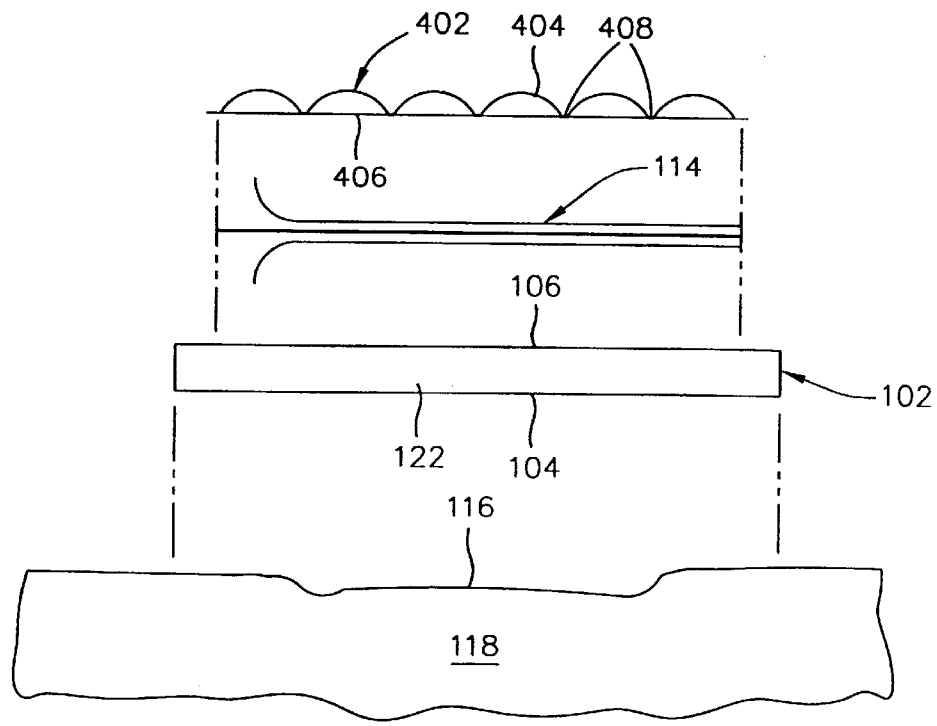
FIG. 33 is an exploded cross-sectional illustration of the FIG. 32 embodiment shown above the wound.
Figure 34:
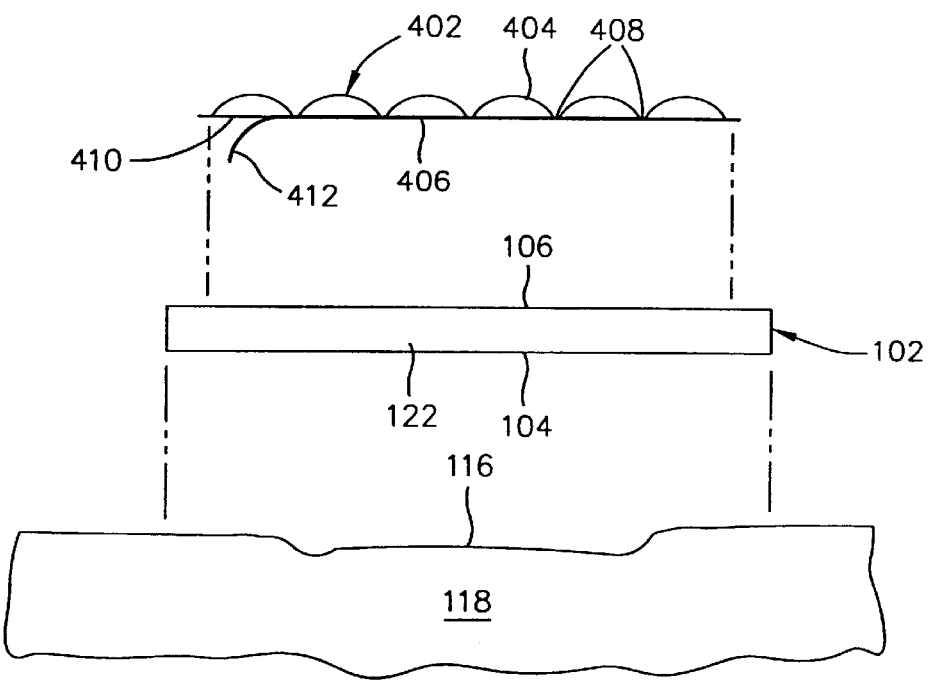
FIG. 34 is an exploded cross-sectional illustration of the FIG. 32 embodiment with an adhesive attachment device applied to the heater.

Still another embodiment 400 of the wound treatment apparatus is illustrated in FIGS. 32–34. In this embodiment a heater 402 employs a chemical or phase-change salt as the means for generating heat to be provided to the bandage 102. As with the embodiments discussed above, these materials are selected to enable the heater 402 to maintain the wound site 116 at or near a normothermic temperature. As shown in FIG. 33, the heater 402 may comprise a pair of polymeric films 404 and 406 which are sealed at their peripheries to provide an enclosure for the chemical or phase change salt. Further, the polymeric films 404 and 406 may be joined by spot thermo-setting at spaced-apart locations 408 for the purpose of lowering the profile of the heater and maintaining the chemical or phase-change salt in discrete confined areas. The film 406 may be stiffer than the film 404. Again, the bandage 102 and the attachment device for attaching the heater 402 to the bandage 102 may be any of the embodiments described hereinabove. The preferred attachment device is the double-sided tape 114, as shown in FIG. 33, which is filly described hereinabove. Alternatively, the heater 402 may be provided with an adhesive layer 410 which is covered by a release liner 412, as shown in FIG. 34.

The invention provides a wound treatment device having a low profile for the convenience of the patient and permitting easy removal of the heater from a bandage without disturbing the attachment of the bandage to the person's body. The bandage, the heater and the attachment device are all flexible and cooperate to conform to the wound to the contour of a person's body where the wound is located so as to permit a substantially hermetic seal about, and moist environment at, the wound site. Numerous attachment embodiments have been described for making the pull strength between the heater 108 and the bandage 102 less than the pull strength between the bandage 102 and the person's body. Even though the bandage 102 is removable, it is desirable to first remove the heater and then to take special care in removing the bandage from the person's body. The invention also enables treatment of the wound and/or the periwound, as desired.

The heater embodiments all enable a wound treatment device according to this invention to maintain the temperature of a wound site at or near a normothermic level. That is to say, the wound treatment device maintains the temperature of tissue in and/or near a wound in a range of about 36° C. to about 38° C.

Clearly, other embodiments and modifications of this invention will occur readily to those of ordinary skill in the art in view of these teachings. Therefore, this invention is to be limited only by the following claims, which include all such embodiments and modifications when viewed in conjunction with the above specification and accompanying drawings.

We claim:

1. A treatment apparatus for enhancing immune function, comprising:

a thermally conductive bandage having first and second surfaces, the first surface of the bandage defining a treatment area for a person's skin;

a pattern of adhesive with a first tack on the first surface;

a heater for maintaining a treatment temperature at (Added) The treatment area; and adhesive with a second tack acting between the heater and the second surface for retaining the heater near the second surface;

the first tack being different than the second tack.

2. The treatment apparatus of claim 1, each of the heater and the bandage being flexible, such that the heater and the second surface are planar when the heater and bandage are unflexed.

3. The treatment apparatus of claim 1, the bandage including a flexible polymeric film and the second surface being a surface of the film.

4. The treatment apparatus of claim 3, the bandage including a layer of a material selected from the group of materials including gauze, hydrogel, and hydrocolloids, the polymeric film being attached to the layer.

5. The treatment apparatus of claim 1, further including:

the bandage including inner and outer boundaries;

the inner boundary defining the wound treatment area; and, the pattern of adhesive located on the first surface between the inner and outer boundaries.

6. The treatment apparatus of claim 5, the bandage including an outer perimeter and the outer boundary substantially approximates the outer perimeter of the bandage.

7. The treatment apparatus of claim 5:

the adhesive including an adhesive device acting between the heater and the second surface;

each of the adhesive device and the pattern of adhesive having a pull strength; and the pull strength of the adhesive device being less than the pull strength of the pattern of adhesive.

8. The treatment apparatus of claim 7, the adhesive device including a plurality of adhesive regions, the adhesive regions being sized and spaced from one another so that the pull strength of the adhesive device is less than the pull strength of the pattern of adhesive.

9. The treatment apparatus of claim 7, the adhesive device including at least one adhesive layer with the second tack, the second tack being less than the first tack.

10. The treatment apparatus of claim 7, the adhesive device including an adhesive layer that is continuous across the treatment area.

11. The treatment apparatus of claim 7, the adhesive device including an adhesive layer that is intermittent across the treatment area.

12. The treatment apparatus of claim 7, the adhesive device being an adhesive layer on the heater, or on the second surface of the bandage.

13. The treatment apparatus of claim 12, the adhesive device including first and second adhesive layers, the first adhesive layer being on the heater and the second adhesive layer being on the second surface of the bandage.

14. The treatment apparatus of claim 13, the first and second adhesive layers bonding when contacting one another.

15. The treatment apparatus of claim 13, the second surface of the bandage including a flexible polymeric film.

16. The treatment apparatus of claim 15, the first and second adhesive layers being bonded to one another.

17. The treatment apparatus of claim 7, the adhesive device being a double-sided tape.

18. The treatment apparatus of claim 17, the double-sided tape including a flexible polymeric film with first and second surfaces, the double-sided tape further including a first adhesive layer on the first surface of the polymeric film and a second adhesive layer on the second surface of the polymeric film.

19. The treatment apparatus of claim 1, the heater including means for applying heat across substantially the entire wound treatment area.

20. The treatment apparatus of claim 1, the heater including means for applying heat across at least a portion of the treatment area.

21. The treatment apparatus of claim 1, the heater including:

a pouch; and means for generating heat located within the pouch.

22. The treatment apparatus of claim 21, the means for generating heat including water.

23. The treatment apparatus of claim 21, the means for generating heat including a chemically reactive material.

24. The treatment apparatus of claim 21, the means for generating heat including a phase-change salt.

25. The treatment apparatus of claim 21, the heater including an electrical resistance element.

26. The treatment apparatus of claim 25, the electrical resistance element disposed for generating heat across at least a portion of the heater.

27. The treatment apparatus of claim 26, the electrical resistance element disposed for generating heat in a region of the heater.

28. The treatment apparatus of claim 25, the electrical resistance element disposed for generating heat in only a portion of the heater.

29. The treatment apparatus of claim 28, the electrical resistance element disposed for generating heat only in a peripheral region of the heater.

30. The treatment apparatus of claim 25, the heater including:
   a flexible layer; and
   the electrical resistance element being embedded in the flexible layer.

31. The treatment apparatus of claim 30, the flexible layer being a polymer.

32. The treatment apparatus of claim 1, further including:
   inner and outer boundaries on the first surface of the bandage, the inner boundary defining the treatment area;
   a pattern of adhesive located between the inner and outer boundaries; and
   the attachment means including an adhesive device having at least one adhesive layer that substantially fills the treatment area.

33. The treatment apparatus of claim 32, further including:
   each of the adhesive device and the pattern of adhesive having a pull strength; and
   the pull strength of the adhesive device being less than the pull strength of the pattern of adhesive.

34. The treatment apparatus of claim 33, the heater being dispose for applying heat across substantially the entire treatment area.

35. The treatment apparatus of claim 34, each of the heater and the bandage being flexible, with the heater and the second surface being substantially planar in a nonflexed state.

36. The treatment apparatus of claim 35, the second surface of the bandage including a flexible polymeric film.

37. The treatment apparatus of claim 36, the heater including:
   a pouch; and
   means for generating heat located within the pouch.

38. The treatment apparatus of claim 36, the heater including:
   a flexible layer; and
   an electrical resistance element being embedded in the flexible layer.

39. The treatment apparatus of claim 38, the adhesive device including:
   a flexible polymeric film with first and second surfaces; and
   first and second adhesive layers, the first adhesive layer being on the first surface of the polymeric film and the second adhesive layer being on the second surface of the polymeric film.

40. The treatment apparatus of claim 36, the adhesive device including a plurality of adhesive regions, the adhesive regions being sized and spaced from one another so that the pull strength of the adhesive device is less than the pull strength of the pattern of adhesive.

41. The treatment apparatus of claim 36, the adhesive device including at least one adhesive layer with a tack, the tack of the at least one adhesive layer of the adhesive device being than the tack of the pattern of adhesive.

42. The treatment apparatus of claim 36, the adhesive device being an adhesive layer on one of the heater and the second surface of the bandage.

43. The treatment apparatus of claim 42, the adhesive device including first and second adhesive layers, the fast adhesive layer being on the first surface of the heater and the second adhesive layer being on the second surface of the bandage.

44. The treatment apparatus of claim 42, the first and second adhesive layers being bonded when contacting one another.

45. The treatment apparatus of claim 42, the first and second adhesive layers capable of bonding to one another but not to the polymeric film surface of the bandage.

46. The treatment apparatus of claim 42, the adhesive device being a double-sided tape.

47. The treatment apparatus of claim 46, the double-sided tape including a flexible polymeric film with first and second surfaces, the double-sided tape further including a first adhesive layer on the first surface of the polymeric film and a second adhesive layer on the second surface of the polymeric film.

48. The treatment apparatus of claim 1, further including a controller for causing the heater to maintain the treatment temperature.

49. The treatment apparatus of claim 48, the controller including means for causing the heater to perform a cycling therapy operation.

* * * * *

UNITED STATES PATENT AND TRADEMARK OFFICE
CERTIFICATE OF CORRECTION

| | | |
|---|---|---|
| PATENT NO. | : 6,585,670 B2 | Page 1 of 1 |
| APPLICATION NO. | : 10/196875 | |
| DATED | : July 1, 2003 | |
| INVENTOR(S) | : Augustine et al. | |

It is certified that error appears in the above-identified patent and that said Letters Patent is hereby corrected as shown below:

IN THE CLAIMS
Column 11
Claim 1, line 52
Delete " (Added) "

Signed and Sealed this

Fourth Day of September, 2007

JON W. DUDAS
*Director of the United States Patent and Trademark Office*